US012653377B2

(12) United States Patent
Ye et al.

(10) Patent No.: US 12,653,377 B2
(45) Date of Patent: Jun. 16, 2026

(54) CALIBRATION OF CAMERA AND LOCATION SENSOR

(71) Applicant: Auris Health, Inc., Santa Clara, CA (US)

(72) Inventors: Menglong Ye, Mountain View, CA (US); Elif Ayvali, Redwood City, CA (US); Austin Jun Shin, Redwood City, CA (US); Bryan Zhao, San Francisco, CA (US); David Paul Noonan, San Francisco, CA (US)

(73) Assignee: Auris Health, Inc., Santa Clara, CA (US)

( * ) Notice: Subject to any disclaimer, the term of this patent is extended or adjusted under 35 U.S.C. 154(b) by 68 days.

(21) Appl. No.: 18/725,759

(22) PCT Filed: Dec. 20, 2022

(86) PCT No.: PCT/IB2022/062530
§ 371 (c)(1),
(2) Date: Jun. 29, 2024

(87) PCT Pub. No.: WO2023/126769
PCT Pub. Date: Jul. 6, 2023

(65) Prior Publication Data
US 2024/0423448 A1 Dec. 26, 2024

Related U.S. Application Data

(60) Provisional application No. 63/295,512, filed on Dec. 30, 2021.

(51) Int. Cl.
A61B 1/00 (2006.01)
A61B 34/30 (2016.01)
(Continued)

(52) U.S. Cl.
CPC ...... *A61B 1/00057* (2013.01); *A61B 1/00149* (2013.01); *A61B 34/30* (2016.02);
(Continued)

(58) Field of Classification Search
CPC ........... A61B 1/00006; A61B 1/00057; A61B 1/00059; A61B 1/00149; A61B 1/0016;
(Continued)

(56) References Cited

U.S. PATENT DOCUMENTS

2016/0374541 A1* 12/2016 Agrawal ............ A61B 1/00149
600/102
2019/0290109 A1* 9/2019 Agrawal ............ A61B 1/00006
(Continued)

FOREIGN PATENT DOCUMENTS

CN 113520603 A 10/2021

OTHER PUBLICATIONS

Adjoint Transformation Algorithm for Hand-Eye (Year: 2017).*
(Continued)

*Primary Examiner* — Md N Haque
(74) *Attorney, Agent, or Firm* — Paradice & Li LLP

(57) ABSTRACT

The present disclosure relates to systems, devices, and methods to calibrate an endoscope with a location-sensor-to-camera transform or a camera-to-location-sensor transform.

20 Claims, 10 Drawing Sheets

(51) Int. Cl.

| | |
|---|---|
| *A61B 90/98* | (2016.01) |
| *A61B 1/04* | (2006.01) |
| *A61B 34/20* | (2016.01) |

(52) U.S. Cl.

CPC ................ *A61B 90/98* (2016.02); *A61B 1/04* (2013.01); *A61B 2034/2065* (2016.02); *A61B 2560/0233* (2013.01); *A61B 2560/0238* (2013.01)

(58) Field of Classification Search

CPC ............ A61B 1/04; A61B 2017/00725; A61B 2034/2048; A61B 2034/2051; A61B 2034/2061; A61B 2034/2065; A61B 2034/301; A61B 2560/0233; A61B 2560/0238; A61B 34/30; A61B 90/361; A61B 90/98

See application file for complete search history.

(56) References Cited

U.S. PATENT DOCUMENTS

| | | |
|---|---|---|
| 2021/0121250 A1 | 4/2021 | Uesugi |
| 2021/0290317 A1* | 9/2021 | Sen .......................... G06N 3/09 |

2021/0338054 A1    11/2021   Halderman et al.

OTHER PUBLICATIONS

International Search Report and Written Opinion, dated Mar. 31, 2023, from PCT/IB2022/062530, pp. 1-8.

Notification, International Preliminary Report on Patentability, dated Jul. 11, 2024, from PCT/IB2022/062530, pp. 1-6.

Özgüner et al., "Camera-Robot Calibration for the Da Vinci Robotic Surgery System," HHS Public Access, Author Manuscript, IEEE Transactions on Automation Science and Engineering, 17(4), pp. 2154-2161, Oct. 2020.

Pachtrachai et al., "Adjoint Transformation Algorithm for Hand-Eye Calibration with Applications in Robotic Assisted Surgery," Annals of Biomedical Engineering, 46, pp. 1606-1620, 2018.

Extended European Search Report and Opinion from European Patent Application No. 22915312.7, dated Dec. 4, 2025, 11 pages.

Lai, M., Shan, C., & de With, P. H. (Sep. 2018). Hand-eye camera calibration with an optical tracking system. In Proceedings of the 12th International Conference on Distributed Smart Cameras 7 pages.

Tabb, A., & Ahmad Yousef, K. M. (2017). Solving the robot-world hand-eye(s) calibration problem with iterative methods. Machine Vision and Applications, 28(5), 569-590.

* cited by examiner

Figure 3:
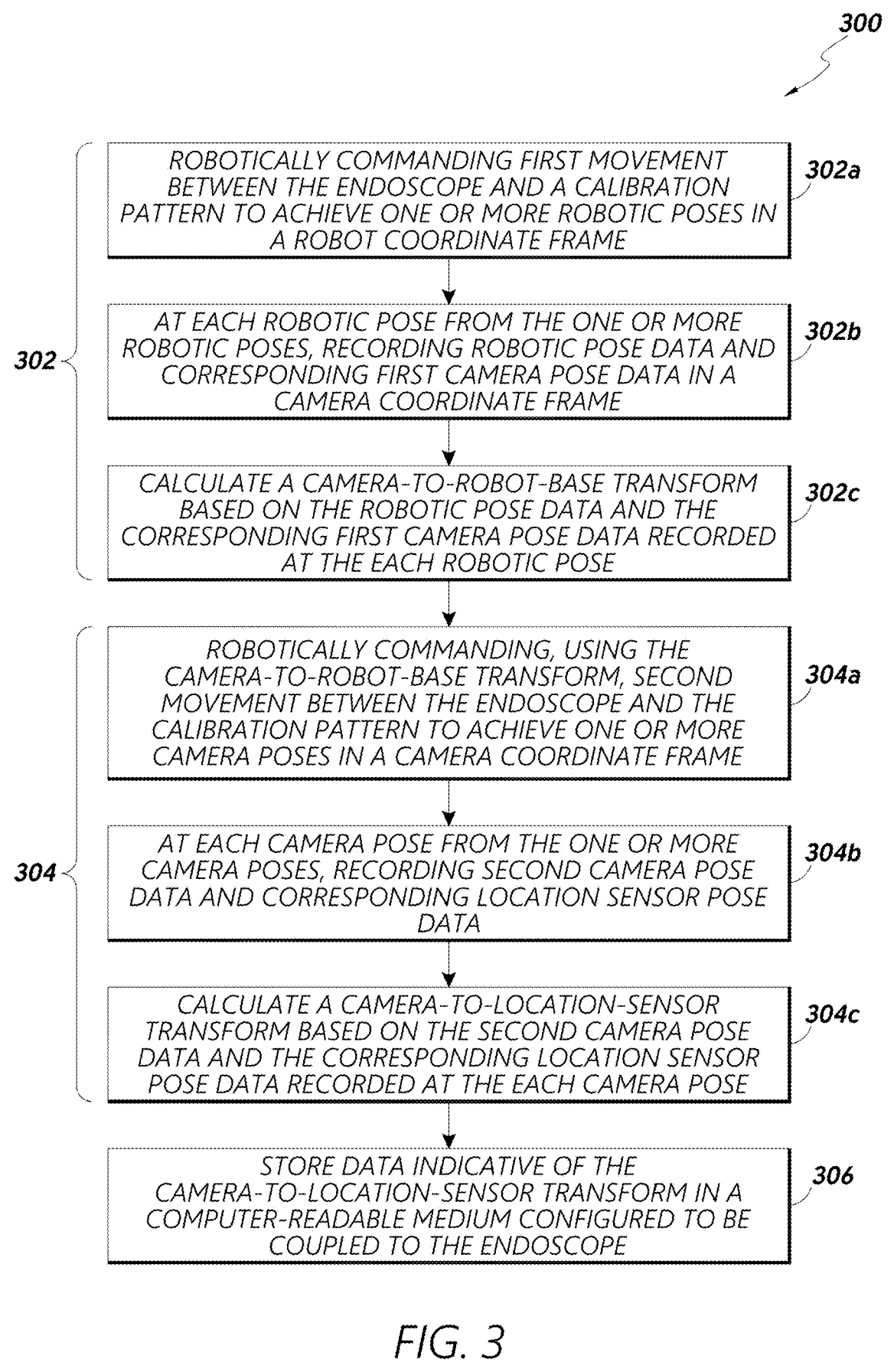

ROBOTICALLY COMMANDING FIRST MOVEMENT BETWEEN THE ENDOSCOPE AND A CALIBRATION PATTERN TO ACHIEVE ONE OR MORE ROBOTIC POSES IN A ROBOT COORDINATE FRAME — *302a*

AT EACH ROBOTIC POSE FROM THE ONE OR MORE ROBOTIC POSES, RECORDING ROBOTIC POSE DATA AND CORRESPONDING FIRST CAMERA POSE DATA IN A CAMERA COORDINATE FRAME — *302b*

CALCULATE A CAMERA-TO-ROBOT-BASE TRANSFORM BASED ON THE ROBOTIC POSE DATA AND THE CORRESPONDING FIRST CAMERA POSE DATA RECORDED AT THE EACH ROBOTIC POSE — *302c*

304 {

ROBOTICALLY COMMANDING, USING THE CAMERA-TO-ROBOT-BASE TRANSFORM, SECOND MOVEMENT BETWEEN THE ENDOSCOPE AND THE CALIBRATION PATTERN TO ACHIEVE ONE OR MORE CAMERA POSES IN A CAMERA COORDINATE FRAME — *304a*

AT EACH CAMERA POSE FROM THE ONE OR MORE CAMERA POSES, RECORDING SECOND CAMERA POSE DATA AND CORRESPONDING LOCATION SENSOR POSE DATA — *304b*

CALCULATE A CAMERA-TO-LOCATION-SENSOR TRANSFORM BASED ON THE SECOND CAMERA POSE DATA AND THE CORRESPONDING LOCATION SENSOR POSE DATA RECORDED AT THE EACH CAMERA POSE — *304c*

STORE DATA INDICATIVE OF THE CAMERA-TO-LOCATION-SENSOR TRANSFORM IN A COMPUTER-READABLE MEDIUM CONFIGURED TO BE COUPLED TO THE ENDOSCOPE — *306*

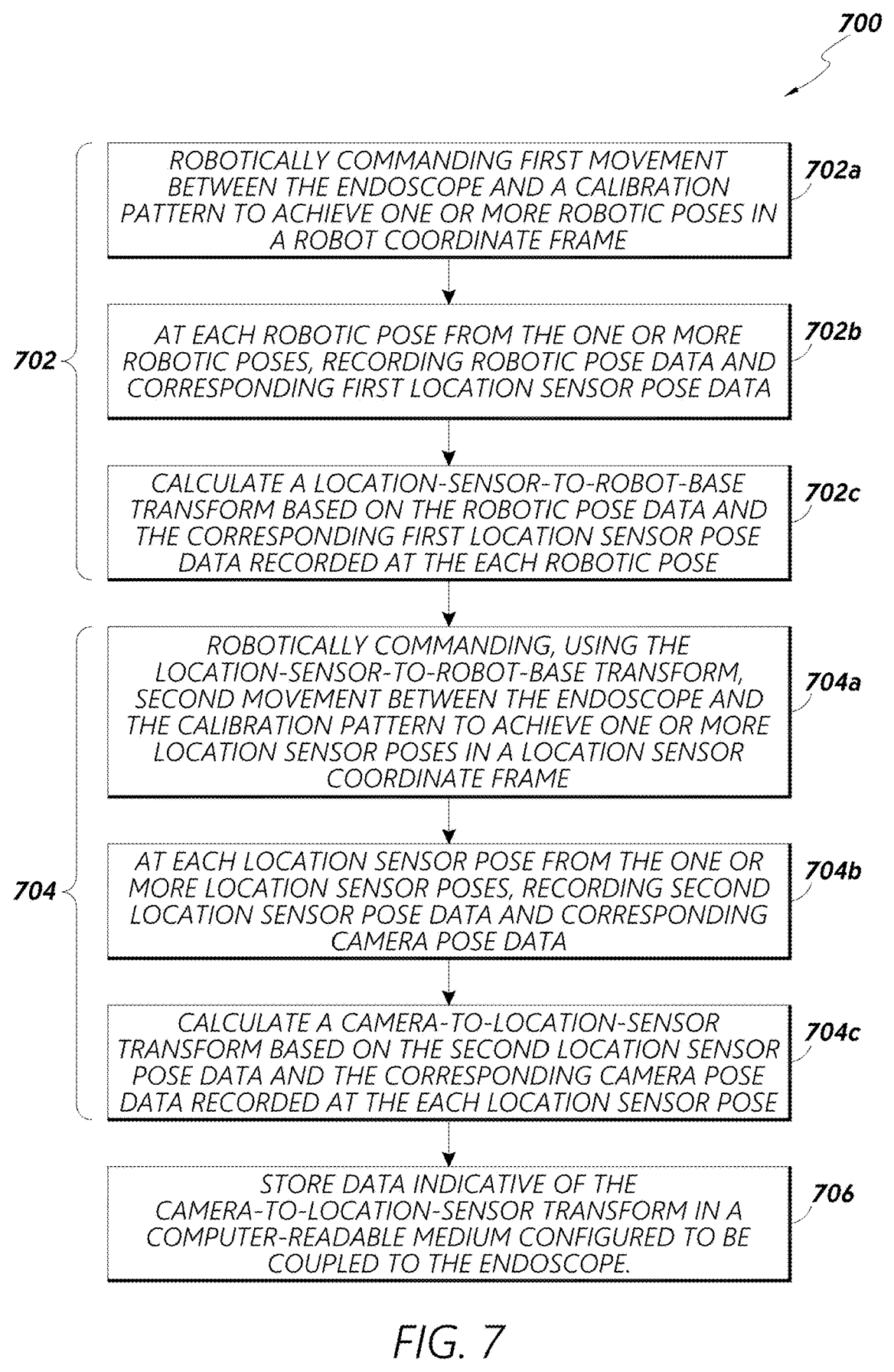

*702a* ROBOTICALLY COMMANDING FIRST MOVEMENT BETWEEN THE ENDOSCOPE AND A CALIBRATION PATTERN TO ACHIEVE ONE OR MORE ROBOTIC POSES IN A ROBOT COORDINATE FRAME

*702b* AT EACH ROBOTIC POSE FROM THE ONE OR MORE ROBOTIC POSES, RECORDING ROBOTIC POSE DATA AND CORRESPONDING FIRST LOCATION SENSOR POSE DATA

*702c* CALCULATE A LOCATION-SENSOR-TO-ROBOT-BASE TRANSFORM BASED ON THE ROBOTIC POSE DATA AND THE CORRESPONDING FIRST LOCATION SENSOR POSE DATA RECORDED AT THE EACH ROBOTIC POSE

*702*

*704a* ROBOTICALLY COMMANDING, USING THE LOCATION-SENSOR-TO-ROBOT-BASE TRANSFORM, SECOND MOVEMENT BETWEEN THE ENDOSCOPE AND THE CALIBRATION PATTERN TO ACHIEVE ONE OR MORE LOCATION SENSOR POSES IN A LOCATION SENSOR COORDINATE FRAME

*704b* AT EACH LOCATION SENSOR POSE FROM THE ONE OR MORE LOCATION SENSOR POSES, RECORDING SECOND LOCATION SENSOR POSE DATA AND CORRESPONDING CAMERA POSE DATA

*704c* CALCULATE A CAMERA-TO-LOCATION-SENSOR TRANSFORM BASED ON THE SECOND LOCATION SENSOR POSE DATA AND THE CORRESPONDING CAMERA POSE DATA RECORDED AT THE EACH LOCATION SENSOR POSE

*704*

*706* STORE DATA INDICATIVE OF THE CAMERA-TO-LOCATION-SENSOR TRANSFORM IN A COMPUTER-READABLE MEDIUM CONFIGURED TO BE COUPLED TO THE ENDOSCOPE.

*FIG. 7*

CALIBRATION OF CAMERA AND LOCATION SENSOR

PRIORITY APPLICATION(S)

This application is a National Stage Entry filed under 35 U.S.C. § 371 of PCT/IB2022/062530, filed Dec. 20, 2022, entitled CALIBRATION OF CAMERA AND LOCATION SENSOR, which claims priority to U.S. Provisional Application No. 63/295,512, filed Dec. 30, 2021, entitled CALIBRATION OF CAMERA AND LOCATION SENSOR, the disclosures of which are hereby incorporated by reference in their entireties.

BACKGROUND

Various medical procedures involve the use of one or more devices configured to penetrate the human anatomy to reach a treatment site. Certain operational processes can involve localizing a medical instrument within the patient and visualizing an area of interest within the patient. To do so, many medical instruments may include sensors to track the location of the instrument and may include vision capabilities, such as embedded cameras or the compatible use with vision probes.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIGS. 2A, 2B, and 2C are diagrams illustrating different exemplary embodiments of the calibration control platform that provide robotic and/or manual control during the calibration procedure.

FIG. 3 is a block diagram showing a method for automatically calibrating an endoscope such that, for example, a transform between the coordinate frames for a location sensor and camera is determined in accordance with one or more embodiments.

FIG. 7 is a block diagram showing a method for automatically calibrating an endoscope such that, for example, a transform between the coordinate frames for a location sensor and camera is determined in accordance with one or more embodiments.

DETAILED DESCRIPTION

Figure 1:
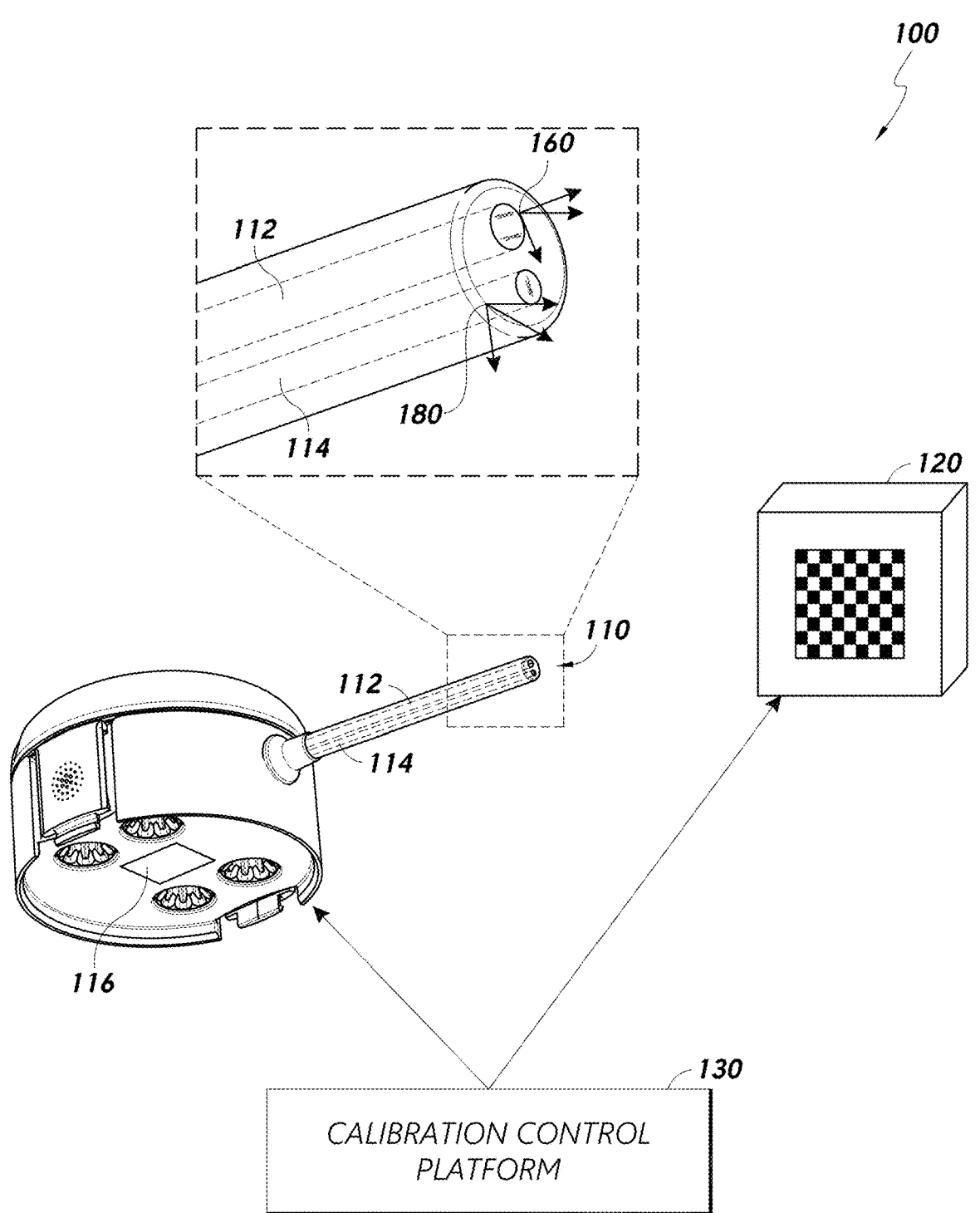
FIG. 1 is a diagram illustrating an automatic calibration system, according to an example embodiment.

The headings provided herein are for convenience only and do not necessarily affect the scope or meaning of disclosure. Although certain exemplary embodiments are disclosed below, the subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

The present disclosure relates to systems, devices, and methods to calibrate an endoscope. For example, an endoscope can be manufactured with multiple sensors, including robot encoders, location sensors, and camera sensors. As the readings from different sensors will be represented in their respective coordination frames, this disclosure contemplates a calibration for generating a transform or transforms between the coordination frames of two or more of these sensors, such as a location sensor and a camera sensor. As used herein, a transform (interchangeably referred herein as a "transformation") may be data that provides a mapping between locations across multiple coordinate frames. In some cases, the transforms discussed herein may be uni-directional such that a transform only provides a mapping from a location in one coordinate frame to another, but not vice versa. In other cases, the transforms discussed herein may be bi-directional such that the transform allows a mapping from a location from a first coordinate frame to a location in a second coordinate frame and vice versa (e.g., a location from the second coordinate frame to a location in the first coordinate frame). The transform maps locations in the location sensor coordinate frame to the locations in the camera coordinate frame (and possibly vice versa) is referred to as a "location-sensor-to-camera" transform or a "camera-to-location-sensor" transform. A location-sensor-to-camera transform may be useful in allowing the readings (e.g., positions and rotations) from one sensor (e.g., the location sensor or the camera sensor) to be mapped to readings in the other coordinate frame. Further, this calibration that generates a location-sensor-to-camera transform may be useful in allowing the readings from either or both of the sensors to be used in a unified coordination system, such as a robotic coordinate system. Further yet, some embodiments automate at least some aspects of calibrating the endoscope, which may be useful in calibrating robotic endoscopes in an industrial setting.

Automatic Endoscope Calibration

FIG. 1 is a diagram illustrating an automatic calibration system 100, according to an example embodiment. The automatic calibration system 100 may include an endoscope 110, a calibration pattern device 120, and a calibration control platform 130. The endoscope 110 may be any suitable medical instrument capable of being coupled to a medical robotic system with capabilities for providing location data and vision data. Accordingly, the term "endoscope," as used herein, can refer to any type of elongate medical instrument having image generating, viewing, and/or capturing functionality instrumented to also include sensor usable to determine a location or shape of the endoscope. An endoscope is also configured to be introduced into any type of organ, cavity, lumen, chamber, and/or space of a body. For example, references herein to scopes or endoscopes can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, and so on.

As shown in FIG. 1, the endoscope 110 may include a camera 112, a location sensor 114, and a calibration data store 116. The camera 112 may be any suitable device capable of providing vision capabilities to the endoscope, such as, by way of example and not limitation, a camera, a fluoroscope, or the like. The camera may be integrated in the instrument itself or may be provided as a removable probe through a working channel of the endoscope.

The location sensor 114 may be any suitable sensor (or sensors) capable of providing location or motion data regarding the endoscope. Example of location sensors include, but are not limited to: electromagnetic (EM) sensors, shape sensing fibers, gyroscopes, accelerometers, magnetometers, or the like. As with the camera 112, the location sensor 114 may be integrated directly in the endoscope or may be provided as a removable probe through the working channel of the endoscope.

As the callout in FIG. 1 shows, the camera 112 and location sensor 114 each have their own respective coordinate frames. For example, the camera 112 has a camera coordinate frame 160 and the location sensor 114 has a location sensor coordinate frame 180. Although each of the coordinate frames 160, 180 may roughly be axially aligned with the tip of the endoscope 110, it should be appreciated that, because of manufacturing differences, for example, there may be slight misalignments with each of the coordinate frames 160, 180. Embodiments described herein attempt to resolve these differences by generating location-sensor-to-camera transforms to allow for positions and orientations in one coordinate frame to be mapped to the other, or in some cases, to a universal coordinate frame, such a robotic coordinate frame.

The calibration data store 116 may be a computer-readable medium configured to store, among other things, data indicative of the location-sensor-to-camera transform. Further, in some embodiments, the calibration data store 116 may be configured to interface with a medical robotic system to communicate the location-sensor-to-camera transform to the medical robotic system. The communication between the calibration data store 116 and a medical robotic system can be a wireless communication or a wired communication. Examples of the calibration data store 116 include radio frequency identification (RFID), USB, FireWire, Ethernet, ATA/IDE, SCSI, PCI, and any other suitable communication protocol. As shown in FIG. 1, the calibration data store 116 may be coupled to the instrument handle of the endoscope. As used herein, an "instrument handle" may refer to a base portion of the endoscope that is configured to be removably coupled to a robotic medical system. The instrument handle may include input elements for steering and actuating the instruments that are driven by output elements of the robotic medical system.

The calibration pattern device 120 may be a device with a known or determinable visual pattern. It is to be appreciated that although FIG. 1 shows the calibration pattern device 120 as having a checkerboard pattern, this disclosure is not so limited. Other embodiments may include other types of visual indicators. For example, the calibration pattern device 120 may include any type of visual indicator with features that are readily discernable via vision processing algorithm. In some embodiments, the calibration pattern device 120 may further include an EM field generator. This may be useful where the location sensor 114 is an EM sensor because having the pattern and the EM field generator in the same calibration pattern device 120 aligns both the line of sight for the camera 112 and the location sensor 114 with the calibration pattern device 120 which may be useful in the calibration steps described in greater detail below.

The calibration control platform 130 may be a platform that facilitates the process of calibrating the endoscope, namely generating a location-sensor-to-camera transform and causing the location-sensor-to-camera transform to be transferred and otherwise stored in the endoscope. As will be discussed in greater detail, the calibration control platform 130 may provide mechanical features and control circuitry for placing the endoscope 110 (and, in turn, the camera 112 and the location sensor 114) and the calibration pattern device 120 in determinable positions relative to each other. The calibration control platform 130 may also include control circuitry for recording location sensor pose data and camera pose data and then calculating the location-sensor-to-camera transform therefrom. As used herein, a "location sensor pose" may refer to some element of a pose (e.g., position and/or orientation) in a coordinate frame of the location sensor. The coordinate frame of the location sensor may be dictated by a tracking modality utilized by location sensor 114 of the endoscope 110. For example, for EM sensors, the coordinate frame may be dictated by the 6 degree of freedom (DOF) readings from the sensor within an EM field generated by an EM field generator embodied in the calibration pattern device 120 or in a stand-alone device. As another example, for shape sensing fibers, the coordinate frame may be dictated by the shape data from the shape sensing fiber relative to a known position, such as a base of the shape sensing fiber, as may be located in the handle of the endoscope or elsewhere.

In comparison, a "camera pose" may refer to some element of a pose (e.g., position and/or orientation) in a coordinate frame of the camera. The coordinate frame of the camera may be based on a vision algorithm operated on images obtained by the camera. Further, the camera coordinate frame may also be influenced by a camera calibration that measures properties of the camera, such as principal points and focal lengths and distortion factors.

Although not shown, the calibration control platform 130 may also include control circuitry for transferring data indicative of the location-sensor-to-camera transform to the calibration data store 116 of the endoscope 110.

Figure 2A:
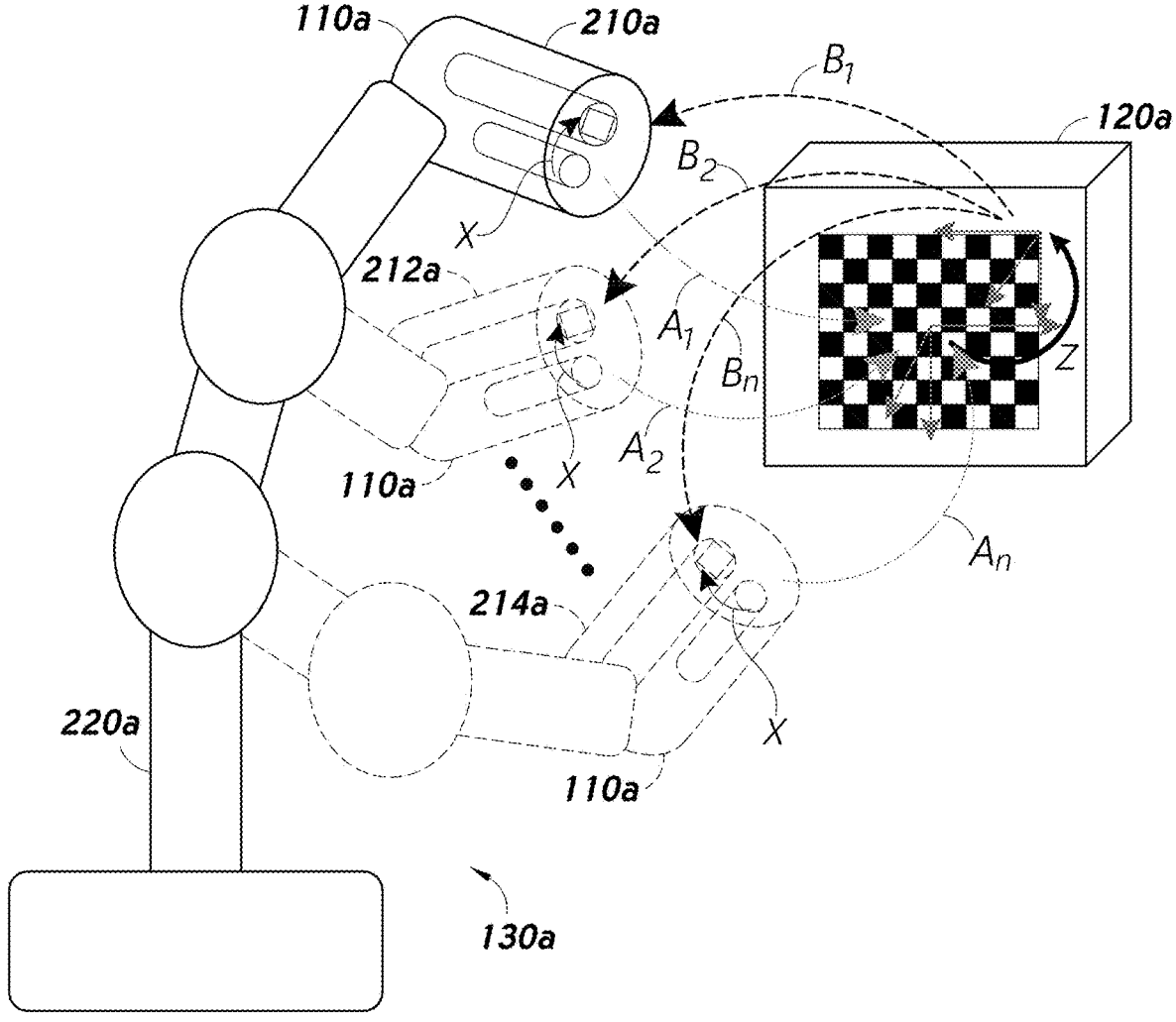
Figure 2B:
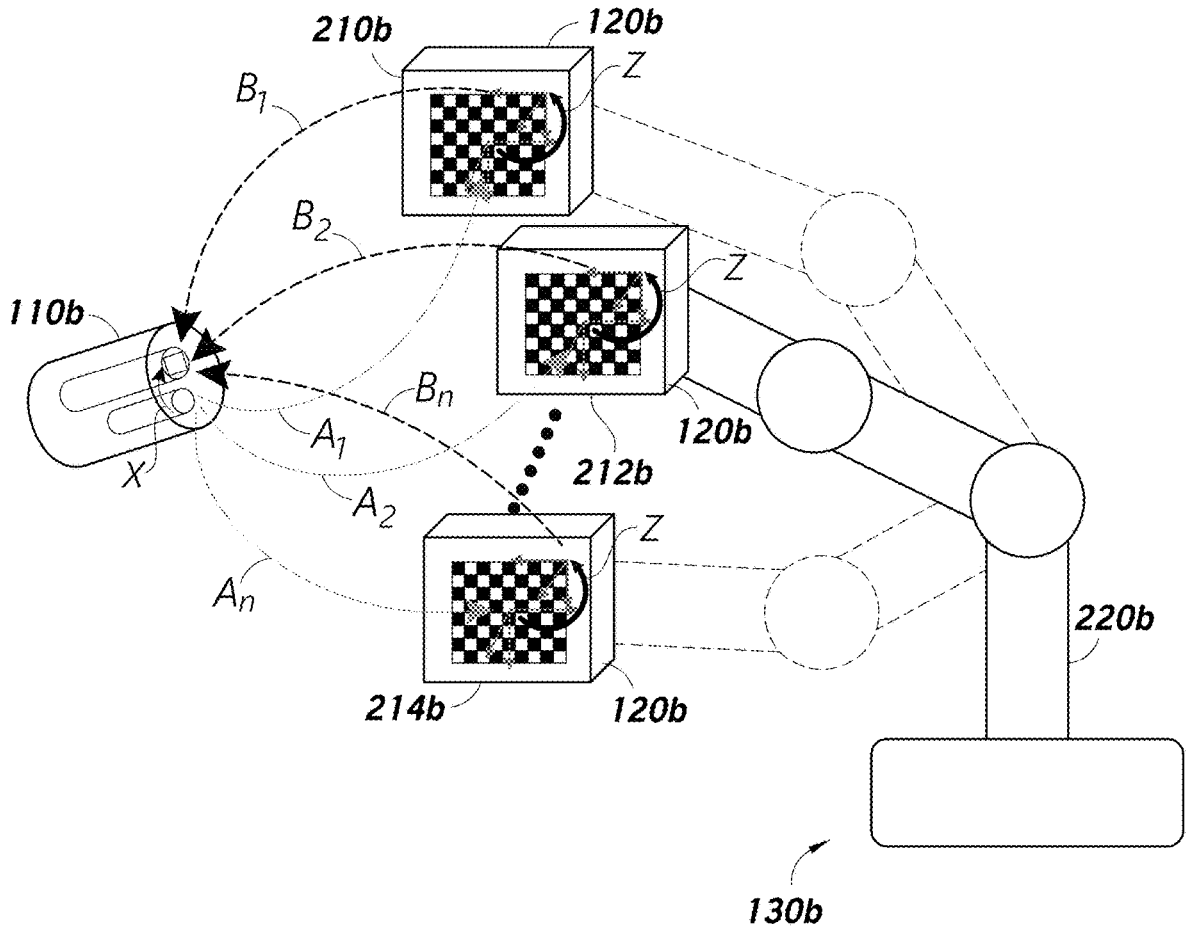

FIGS. 2A and 2B are diagrams illustrating two different exemplary embodiments of the calibration control platform 130a that provide robotic control during the calibration procedure. For example, FIG. 2A illustrates an embodiment where the calibration control platform 130a includes a robotic arm 220a capable of robotically positioning the endoscope 110a relative to the calibration pattern device 120a in a number of determinable poses (e.g., 210a, 212a,

214a). The calibration control platform 130a may include control circuitry configured to record the location sensor pose data and the camera pose data at each of the positions to form a dataset that includes pairs of sensor pose data and camera pose data, each pair corresponding to a different pose (e.g., 210a, 212a, 214a). From the dataset, the control circuitry of the calibration control platform 130a may calculate the location-sensor-to-camera transform and cause data indicative of the location-sensor-to-camera transform to be stored on a computer-readable medium (e.g., the calibration data store 116 of FIG. 1) configured to be coupled to the endoscope 110a.

In contrast, FIG. 2B illustrates an embodiment where a calibration control platform 130b includes a robotic arm 220b that robotically positions a calibration pattern device 120b relative to the endoscope 110b in a number of determinable poses (e.g., 210b, 212b, 214b). The calibration control platform 130b then operates similar to the calibration control platform 130a of FIG. 2A. That is, the control circuitry of the calibration control platform 130b may be configured to record the location sensor pose data and the camera pose data at each of the positions to form a dataset that includes pairs of sensor pose data and camera pose data, each pair corresponding to a different pose (e.g., 210b, 212b, 214b). From the dataset, the control circuitry of the calibration control platform 130b may calculate the location-sensor-to-camera transform and cause data indicative of the location-sensor-to-camera transform to be stored on a computer-readable medium (e.g., the calibration data store 116 of FIG. 1) configured to be coupled to the endoscope 110b.

Figure 2C:
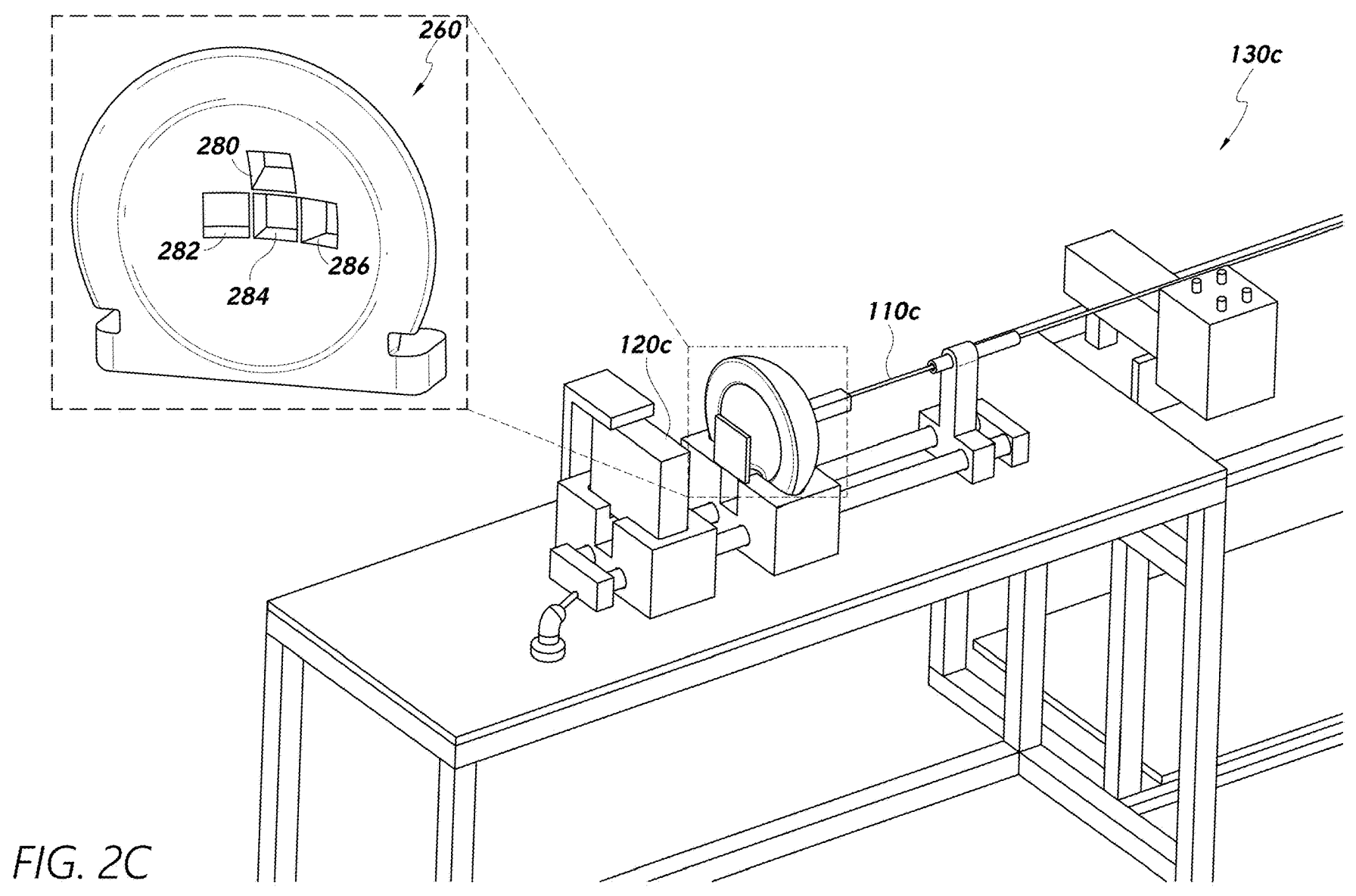

FIG. 2C is a diagram illustrating an example embodiment of a calibration control platform 130c with manual adjustments. For example, the calibration control platform 130c includes a jig 260 with a number of positioning slots 280, 282, 284, 286, a calibration pattern device 120c, and calibration control circuitry. The calibration control circuitry is configured to generate and store the camera pose data and the location sensor pose data from the endoscope 110c, generate a camera-to-location-sensor transform from the stored camera pose data and the location sensor pose data, and transfer data indicative of the camera-to-location-sensor transform to a calibration data store (e.g., the calibration data store 116 shown in FIG. 1).

To generate a camera-to-location-sensor transform, an operator performs an approach of iteratively positioning the endoscope 110c in a number of different positions using the positioning slots 280, 282, 284, 286 of the jig 260. Each of the positioning slots 280, 282, 284, 286 stabilizes the endoscope in different configurations relative to the calibration control platform 130c. At each iteration of the positioning of the endoscope 110c in a different positioning slot, the calibration control circuitry captures and stores the camera pose data and the location sensor pose data at that particular positioning slot.

In some embodiments, the iterations of positioning the endoscope 110c in each of the slots 280, 282, 284, 286 is performed for one or more sides of the endoscope. For example, with the endoscope in a given orientation, the endoscope is placed in each of the slots 280, 282, 284, 286 and with the endoscope in a different orientation, the endoscope is again placed in each of the slots 280, 282, 284, 286, and so forth for any number of orientations.

When the iteration of position the endoscope 110c in the different slots 280, 282, 284, 286 (possibly for multiple orientations of the endoscope 110c) is completed, the calibration control platform 130c then generates the camera-tolocation-sensor transform. Techniques for generating the camera-to-location sensor-transform is discussed in greater detail below.

It is to be appreciated that other embodiments of the calibration control platform are contemplated by this disclosure. For example, an example embodiment consistent with this disclosure includes a calibration control platform that robotically controls both the endoscope and the calibration pattern device to arrive at the determinable poses.

Calibration Methods and Operations

Details of the operations of exemplary automatic calibration systems are now discussed. The methods and operation disclosed herein are described relative to an automatic calibration system 100 shown in FIG. 1. However, it is to be appreciated that the methods and operations may be performed by any of the components, alone or in combination, discussed herein. Further, the operations of an automatic calibration system are discussed in context of a two-phase approach. However, it is to be appreciated that this disclosure contemplates other embodiments that may use additional phases or any sub-operation or sub-phase disclosed herein, and, as such, this disclosure is not limiting to a two-phase approach.

An automatic calibration system may perform a two-phase approach for automatically calibrating an endoscope (e.g., the endoscope 110 of FIG. 1). In general, a two-phase approach may include a first phase that generates an initial transform (e.g., a camera-to-robot-base transform or a location-sensor-to-robot-base transform) and a second phase that uses the initial transform to servo the endoscope to determinable poses to further generate a final location-sensor-to-camera transform. Example embodiments of this process are now discussed in greater detail.

i. Camera-Based Servo Approaches

FIG. 3 is a block diagram showing a method 300 for automatically calibrating an endoscope such that, for example, a transform between the coordinate frames for a location sensor and camera is determined. As FIG. 3 shows, the method 300 may include a first phase 302. During the first phase 302, the automatic calibration system may generate a camera-to-robot-base transform. The first phase 302 may involve a number of sub-blocks, which collectively represent the first phase 302 of a multiphase approach. For example, the first phase 302 may include sub-blocks 302a, 302b, and 302c. At sub-block 302a, the automatic calibration system may robotically command a first movement between the endoscope and a calibration pattern device (e.g., the calibration pattern device 120 of FIG. 1) to achieve one or more robotic poses in a robot coordinate frame. As used herein, the set of one or more robotic poses may be commanded and expressed using coordinates of the robotic coordinate frame. For example, a robotic controller may issue commands to a robotic arm to move the endoscope to a given location in a robotic coordinate frame (e.g., commands to move to a given x, y, z position and/or yaw, pitch, roll orientation of the robotic coordinate frame). Likewise, a robotic controller may issue commands to a robotic arm to move the calibration pattern device to a given location in a robotic coordinate frame (e.g., commands to move to a given x, y, z position and/or yaw, pitch, roll orientation of the robotic coordinate frame). In some embodiments, the robotic poses may be selected such that that the images captured by the camera at each of the robotic poses captures the entire pattern displayed by a calibration pattern device.

At sub-block 302b, the automatic calibration system may record robotic pose data and corresponding first camera pose data at each of the one or more robotic poses achieved at sub-block 302*a*. As discussed above, the camera pose data may be data that is operable to identify a pose (or at least some aspect thereof) of the camera in the camera coordinate frame. For example, in some embodiments, the automatic calibration system may derive camera pose data from the image data obtained at one of the robotic poses of sub-block 302*a* and extract location information therefrom. In an example embodiment, the automatic calibration system may identify locations of specific features of the calibration pattern represented in the image captured at one of the robotic poses and determines the pose of the camera in the camera coordinate frame based on the feature locations. In another example embodiment, to obtain a current camera pose of the object pattern in the camera coordinate frame, a perspective-n-points algorithm can be used. The inputs of the perspective-n-points algorithm can be the object point locations defined on the pattern and their corresponding locations detected on the image, along with the camera intrinsic parameters (obtained in camera calibration).

Accordingly, the automatic calibration system may store N pairs of robotic pose data and camera pose data, where N is the number of robotic poses achieved at sub-block 302*a*. The robotic pose data stored at sub-block 302*b* may be the robotic pose of the command sent to the robotic controller. In other embodiments, there may be some sensor feedback that estimates the pose of the robotic system, such as external cameras, EM sensors embedded in the robot, and the like.

The automatic calibration system, at sub-block 302*c*, calculates the camera-to-robot-base transform using the pairs of robotic pose data (or transforms thereof) and the corresponding first camera pose data (or transforms thereof), as was recorded at sub-block 302*b*. Although discussed in greater detail elsewhere in this disclosure, generating a camera-to-robot-base transform may involve collecting paired measurements of robotic transforms and pairs of pattern to camera transforms and solving:

$$RX_R = X_R B$$

In this calculation, R represents the relative transforms between robot poses (e.g., $R_1$, $R_2$) in the first phase 302 and may be defined as $R = R_2\_inv * R_1$. Robotic poses may be represented as transformation from a robot base to an end effector (as may be determined using forward kinematics of the robot). B represents a relative transform between camera poses (e.g., $B_1$, $B_2$) in the first phase 302 and can be defined as $B = B_2\_inv * B_1$. Camera poses may be transformations from a camera to visual pattern. Thus, $R_1$ may be the transformation from a robot base to an end effector for the first pose, $B_1$ may be the transformation from camera to visual pattern for the first pose, $R_2$ may be the transformation from the robot base to end effector for the second pose, $B_2$ may be the transformation from the camera to second pose pattern for the second pose. ($R_1$, $B_1$) and ($R_2$, $B_2$) are paired, meaning synchronized. There are also probabilistic methods that use a batch of data where R, B pairs don't have to be synchronized. $X_R$ represents the camera-to-robot-base transform.

During the second phase 304, the automatic calibration system may generate a location-sensor-to-camera transform (or a camera-to-location-sensor transform). The second phase 304 may involve a number of sub-blocks, such as, for example, sub-blocks 304*a*, 304*b*, and 304*c*. At sub-block 304*a*, the automatic calibration system may robotically command, using the camera-to-robot-base transform generated during the first phase 302, a second movement between the endoscope and the calibration pattern device to achieve one or more camera poses in the camera coordinate frame. As previously mentioned, a camera pose may be expressed using coordinates of the camera coordinate frame. For example, the set of one or more camera poses of sub-block 304*a* may be expressed as feature locations of the visual pattern on the calibration pattern device or as object point locations defined on the pattern and their corresponding locations detected on the image, along with the camera intrinsic parameters (obtained in camera calibration).

It is to be appreciated that sub-block 304*a* may operate by commanding robotic motions between the calibration pattern device and the endoscope such that determinable camera poses in the camera coordinate frame are achieved. However, the camera coordinate frame is a different coordinate frame from the robotic coordinate frame. To illustrate this difference, say the automatic calibration system determines that the camera needs to move left 50° in a camera coordinate frame to achieve a desired camera pose. If the automatic calibration system commands to a robotic controller to move left 50° this movement will occur in the robotic coordinate frame and this movement can result in moving the camera left at some other angle in the camera coordinate frame. Thus, in normal operation, a movement needed to move a current camera pose to a desired camera pose does not necessarily translate as the same movement in the robot coordinate frame. The camera-to-robot-base transform facilitates this operation in that the automatic calibration system can map movements in the camera coordinate frame to movements in the robotic coordinate frame. This approach is referred to as a visual servo approach and is described in greater detail below.

At sub-block 304*b*, the automatic calibration system may record second camera pose data and corresponding location sensor pose data at each of the one or more camera poses. As discussed above, the location sensor pose data may be data that is operable to identify a pose (or at least some aspect thereof) of the location sensor in the location sensor coordinate frame. Accordingly, the automatic calibration system may store N pairs of camera pose data and location sensor pose data, where N is the number of camera poses reached at sub-block 304*a*.

At sub-block 304*c* the automatic calibration system calculates a camera-to-location-sensor transform using the pairs of camera pose data (or transforms thereof) and the corresponding location sensor pose data (or transforms thereof), as was recorded at sub-block 304*b*. Generating a camera-to-location-sensor transform may involve collecting paired measurements of field generator to EM transforms and pairs of pattern-to-camera transforms and solving:

$$AX_{C2LS} = X_{C2LS} B$$

Where A represents relative transforms between location sensor poses (e.g., location-sensor-to-field-generator transforms, where the location sensor is an EM sensor) of the second phase 304, B represents the relative transforms between pattern poses of the second phase 304, and $X_{C2LS}$ represents the camera-to-location-sensor transform.

At block 306, the automatic calibration system stores data indicative of the camera-to-location-sensor transform in a computer-readable medium of the endoscope, such as the calibration data store 116 of FIG. 1. As discussed above, with respect to FIG. 1, a calibration data store may be an RFID tag but could be any suitable device capable of storing data indicative of the camera-to-location-sensor transform and then communicating the camera-to-location-sensor transform to a robotic system when the endoscope is coupled to the robotic system. Based on the camera-to-locationsensor transform, any camera pose, location sensor pose, or robotic pose may be specified or otherwise provided in any of the camera coordinate system, location sensor coordinate system, or robotic coordinate system. In some examples, any camera pose, location sensor pose, or robotic pose may be specified or otherwise provided in an EM coordinate frame, which may be the coordinate frame of the location sensor.

Figure 4:
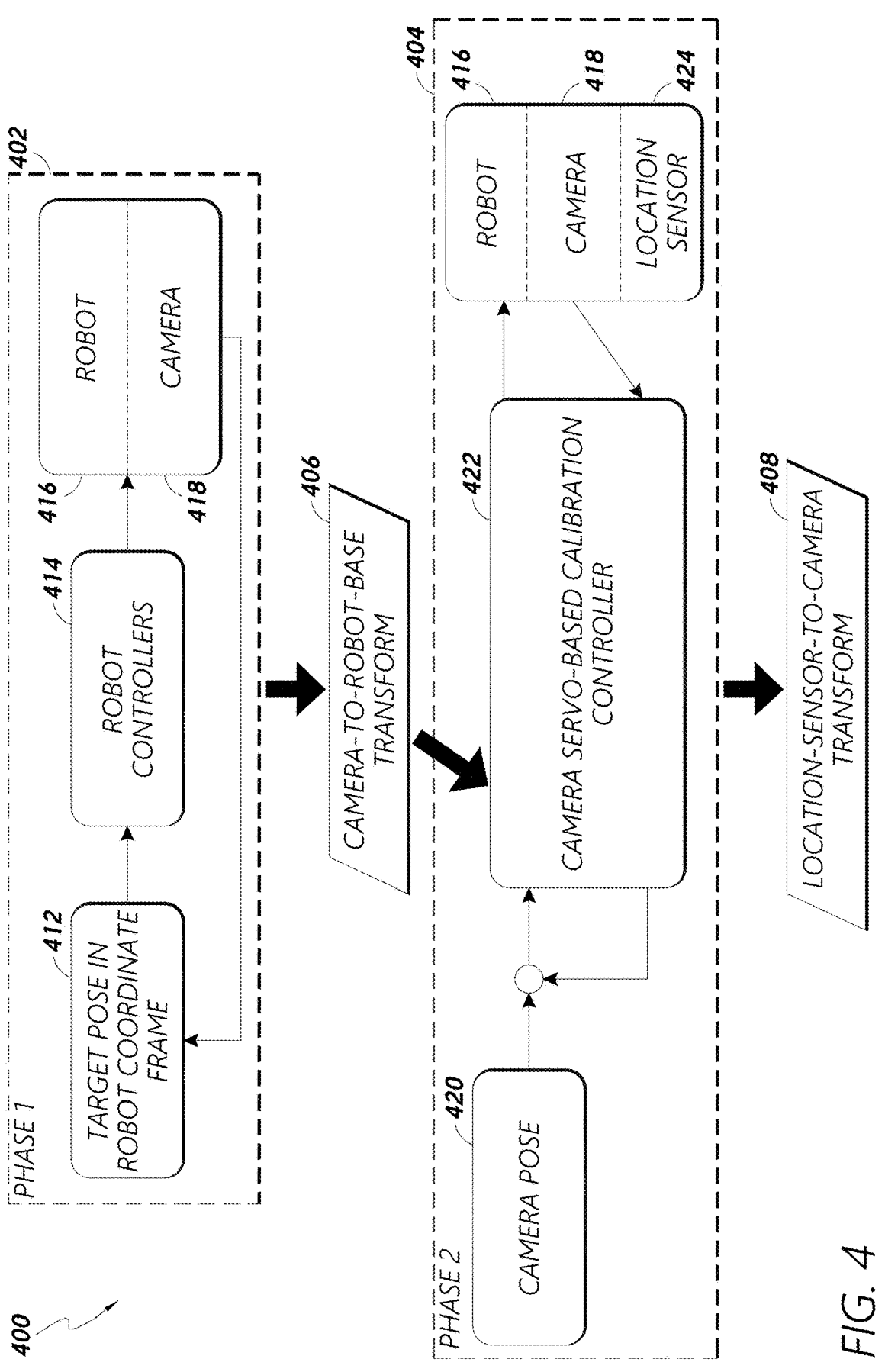
FIG. 4 is a block diagram illustrating an example embodiment of an automatic calibration system implementing the method of FIG. 3.

FIG. 4 is a block diagram illustrating an example embodiment of an automatic calibration system 400 implementing the method 300 of FIG. 3. As FIG. 4 shows, similar to the method 300 of FIG. 3, the automatic calibration system 400 operates to perform multiple phases, a first phase 402 and a second phase 404, where the first phase 402 operates to generate a camera-to-robot-base transform 406 and the second phase 404 operates to generate a location-sensor-to-camera transform 408. In the first phase 402, to obtain the camera-to-robot-base transform 406, a set of robotic poses 412 in the robot coordination frame can be pre-determined empirically. In some embodiments, the pattern may be fully visible in the captured image for each robotic pose of the pre-determined robotic poses 412. For example, the robotic controller 414 may issue commands to the robot 416 to move the endoscope to a given location in the robotic coordinate frame (e.g., commands to move to a given x, y, z position and/or yaw, pitch, roll orientation of the robotic coordinate frame).

After executing each robot pose 412, the corresponding robot pose and camera pose data are recorded. For example, after reaching a robotic pose, the robotic pose data associated with the robotic pose (e.g., the x, y, z and yaw, pitch, roll coordinates of the robotic command) are stored with camera pose data obtained based on an analysis of a calibration pattern (e.g., a calibration pattern from the calibration pattern device 120 of FIG. 1) represented in image data acquired by the camera 418 of the endoscope. With the obtained set of pairs of data, the camera-to-robot-base transform 406 is calculated.

In the second phase 404, a camera servo-based calibration controller 422 uses the camera-to-robot-base transform 406 to perform camera servo-based calibration. In camera servo-based calibration, the automatic calibration system may command robotic movement to perform 6-DOF motion of an endoscope or the calibration pattern device to reach a set of camera poses (e.g., camera poses 420) such that when a camera pose is reached, the corresponding location sensor pose can be recorded. By way of example and not limitation, this disclosure discusses different ways an automatic calibration system can ensure a camera pose is reached. The first approach is referred to as an image-based servo approach, in which the locations of features of the visual pattern of the calibration pattern device are utilized. The second approach is a pose-based servo approach, in which the current camera pose will be estimated from, for example, visual processing of the image and camera intrinsic parameters.

Both the image- and pose-based servo approaches aim to reduce the error between the expected states (locations or poses) and the current states by providing a feedback loop that the system can compare some attributes associated with the current camera pose of the endoscope with the desired camera pose. Further, the camera servo-based calibration controller uses the camera-to-robot-base transform 406 to convert motions needed to achieve a camera pose in a camera coordinate frame to motions in the robot coordinate frame. In this way, control circuitry implementing the control law of the camera servo-based calibration controller (herein referred as a control law module) is capable of generating commands to the robotic controllers of a robotic arm or robotic arms, for example, to effect movement in the robotic coordinate frame that minimizes the differences in a current camera pose and a desired camera pose in the camera coordinate frame.

The corresponding camera pose data (e.g., via camera 418) and location sensor pose data (e.g., via the location sensor 424) are recorded whenever a desired camera pose is reached. With these, the final location-sensor-to-camera transform 408 is calculated by the camera servo-based calibration controller.

By way of example and not limitation, a number of different camera servo-based calibration approaches are now discussed. As briefly described above, in camera servo-based calibration approaches, an automatic calibration system may command 6-DOF motion of an endoscope or calibration pattern device to reach a set of camera poses $$(\text{denoted as } \{B_i\}_{i=1}^n),$$

such that when a camera pose (e.g., $B_i$) is reached, the corresponding location sensor pose (e.g., $A_i$) can be recorded. By way of example and not limitation, this disclosure discusses two ways an automatic calibration system can ensure camera pose $B_i$ is reached. The first approach is an image-based servo approach, in which the features on the checkboard pattern are utilized. The second approach is a pose-based servo approach, in which the current pose will be estimated. Both the image- and pose-based servo approaches aim to reduce the error between the desired poses and the current poses by providing a feedback loop that the system can compare some attributes associated with the current camera pose with the desired camera pose. A control law module of the system then uses the camera-to-robot-base transform to determine a motion in robotic coordinate frame that will effectuate movement that reduces the error in the camera coordinate frame.

Figure 5:
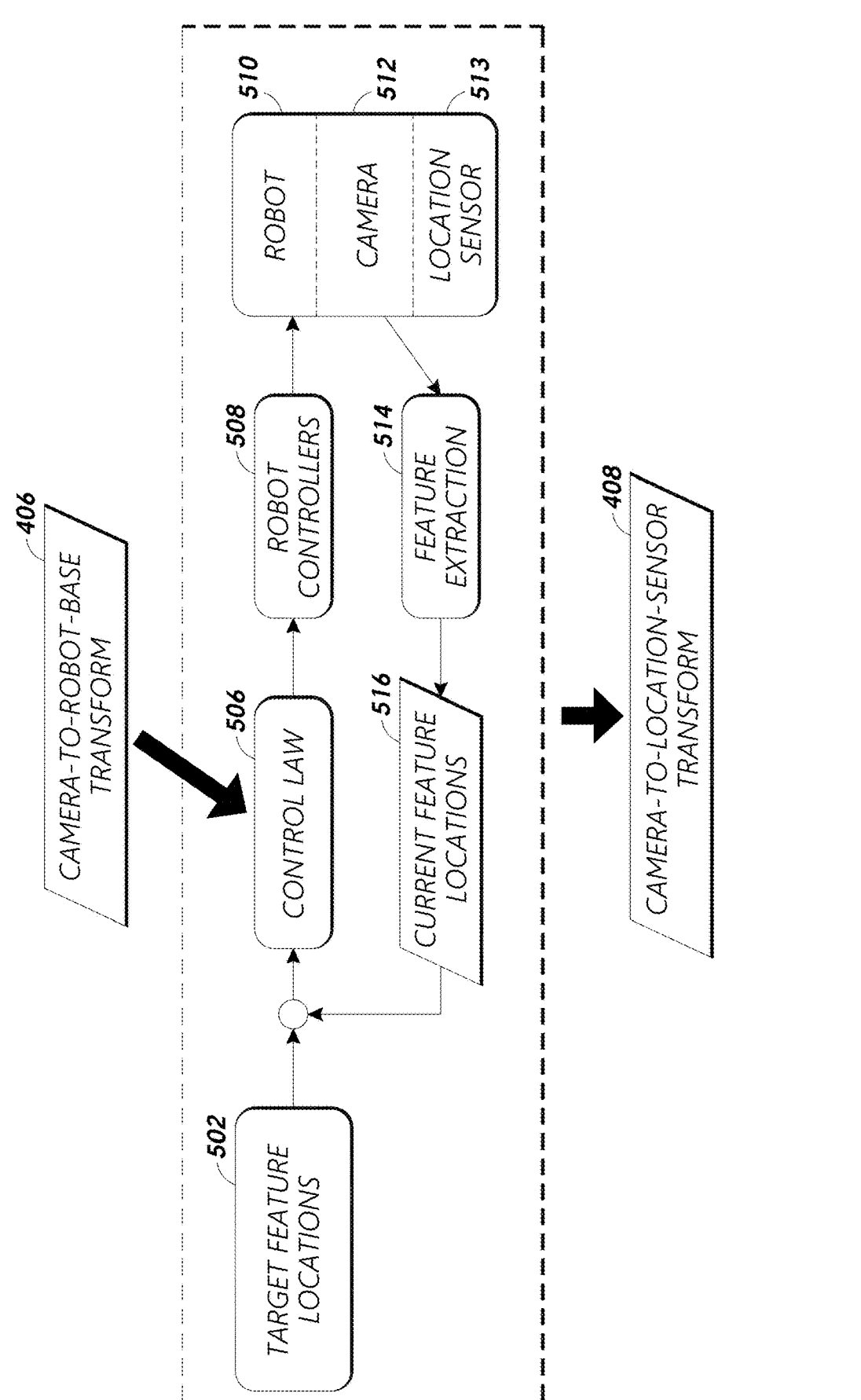
FIG. 5 is a block diagram illustrating image-based visual servo calibration, according to an example embodiment.

FIG. 5 is a block diagram illustrating image-based visual servo calibration, according to an example embodiment.

At block 502, the automatic calibration system selects a target camera pose from a set of camera poses $$(\text{e.g., } \{B_i\}_{i=1}^n).$$

For simplicity of discussion, the target camera pose is referred to as $B_t$. In the image-based visual servo calibration approach, a target camera pose may be expressed in terms of target locations for features in the visual pattern displayed by a calibration pattern device (e.g., the calibration pattern device 120 of FIG. 1).

The control law module 506 receives the target camera pose $B_t$ (e.g., the target locations for features) and a current camera pose $B_c$ and computes a robotic command to achieve robotic movement to reduce the differences between the target camera pose $B_t$ and the current camera pose $B_c$. As shown in FIG. 5, the current feature locations (e.g., the current camera pose $B_c$) is provided as part of a feedback path where a camera sensor 512 (e.g., the camera 112 of FIG. 1) captures an image of the calibration pattern device, features are extracted from the image (see, e.g., block 514), and locations of the extracted features from the current image are determined (see, e.g., block 516). The location information derived from the extracted feature may be referred to as a current camera pose.

It is to be appreciated that the control law module 506 may convert a desired movement in the camera coordinate frame to a desired movement in the robotic coordinate frame. Such a conversion may be obtained using a camera-to-robot-base transform, as may have been determined during an initial calibration setup step (e.g., the first phase in a two-phase calibration approach). The robot controller 508 converts the desired movement in robotic coordinate frame to joint movements in a robotic system. A robot 510 then receives the command and effectuates movement of the robotic system according to the robotic command determined by the control law module 506.

The feedback loop of elements 506, 508, 510, 512, 514, 516 are repeated until the automatic calibration system determines that the current camera pose $B_c$ and the target camera pose $B_t$ are sufficiently similar (e.g., the target feature locations match the current feature locations), as may be determined, for example, by a comparison between the difference in the locations of the image features for both the target camera pose $B_t$ and a threshold amount. Once the automatic calibration system determines that the target pose has been reached, the automatic calibration system may then record the corresponding location sensor data (e.g., $A_i$) from the location sensor 513 while at the target camera pose $B_t$. In some embodiments, the automatic calibration system may record the target camera pose $B_t$ in a data representation different from the data representation used to express the target feature locations. For example, in some embodiments, the 6DOF location of the camera in the camera coordinate frame is determined from the image data when $B_t$ has been reached. Thus, for the set of camera poses, the system will record corresponding location sensor data (from location sensor 513) for those camera poses.

Figure 6:
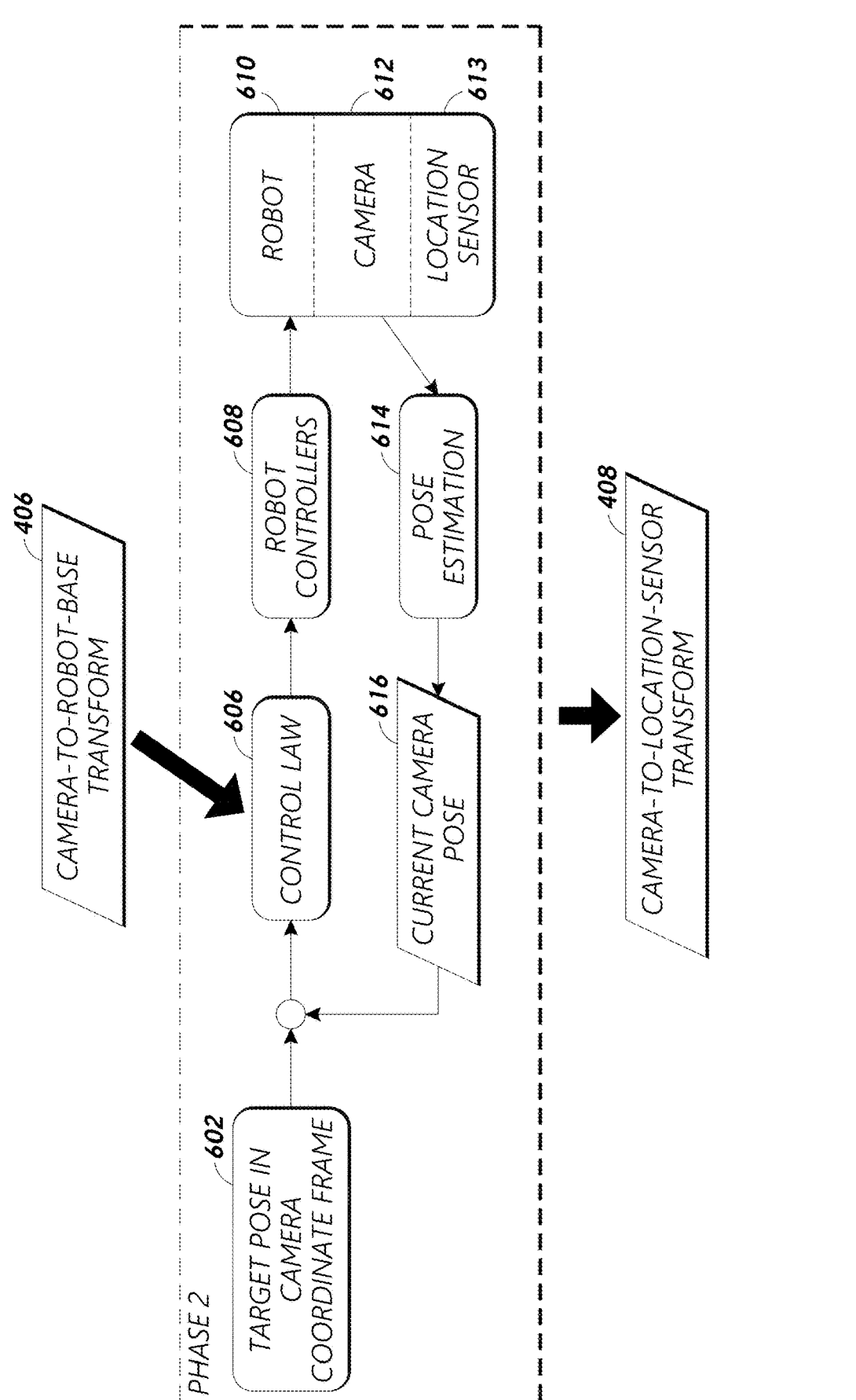
FIG. 6 is a block diagram illustrating a pose-based visual servo calibration approach, according to an example embodiment.

FIG. 6 is a block diagram illustrating a pose-based visual servo calibration approach, according to an example embodiment.

At block 602, the visual servo-based calibration module selects a target camera pose from a set of camera poses $$(e.g., \{B_i\}_{i=1}^n).$$

For simplicity of discussion, the target camera pose is referred to as $B_t$ and may be expressed as a 6DOF positioning of a camera in a camera coordinate frame.

The control law module 606 receives the target camera pose $B_t$ (e.g., the target pose in 6DOF coordinates in the camera coordinate frame) and a current camera pose $B_c$ and computes a robotic command to achieve robotic movement to reduce the differences between the target camera pose $B_t$ and the current camera pose $B_c$. As shown in FIG. 6, the current camera pose $B_c$ is provided as part of a feedback path where a camera sensor 612 (e.g., the camera 112 of FIG. 1) captures an image of a calibration pattern device (e.g., the calibration pattern device 120 of FIG. 1), the current camera pose $B_c$ (e.g., at block 616) is estimated from the image (see, e.g., block 614) and sent to the control law module 606. In some embodiments, the block 614 estimates camera poses based on, for example, a perspective-n-points algorithm. The inputs to the perspective-n-points algorithm may be the object point locations defined on the pattern and their corresponding locations detected on the image, along with the camera intrinsic parameters (obtained from a camera calibration step (not shown)).

It is to be appreciated that the control law module 606 may convert a desired movement in the camera coordinate frame to a desired movement in the robotic coordinate frame. Such a conversion may be obtained using a camera-to-robot-base transform, as may have been determined during an initial calibration setup step (e.g., the first phase in a two-phase calibration approach). The robot controller 608 converts the desired movement in robotic coordinate frame to joint movements in a robotic system. A robot 610 then receives the command and effectuates movement of the robotic system according to the robotic command determined by the control law module 606.

The feedback loop of elements 606, 608, 610, 612, 614, 616 are repeated until the automatic calibration system determines that the current camera pose $B_c$ and the target camera pose $B_t$ are sufficiently similar (e.g., the target pose matches the current pose), as may be determined, for example, by a comparison between the difference in the current camera pose $B_c$ and the target camera pose $B_t$ and a threshold amount. Once the automatic calibration system determines that the target pose has been reached, the automatic calibration system may then record the corresponding location sensor data (e.g., $A_i$) at the target camera pose $B_t$. In some embodiments, the automatic calibration system may record the target camera pose $B_t$ in a data representation different from the data representation used to express the target feature locations. For example, in some embodiments, the 6DOF location of the camera in camera coordinate frame is determined from the image data when $B_t$ has been reached. Thus, for the set of camera poses, the system will record corresponding location sensor data (from location sensor 613) for those poses.

ii. Location Sensor-Based Servo Approaches

In location sensor servo-based calibration, an automatic calibration system may command robotic movement to perform 6-DOF motion to reach a set of location sensor poses $$(denoted\ as\ \{A_i\}_{i=1}^n),$$

such that when a location sensor pose (e.g., $A_i$) is reached, the corresponding camera pose (e.g., $B_i$) can be recorded. Similar to the visual servo-based calibration approaches previously discussed herein, the location sensor servo-based calibration aims to reduce the error between the desired states (locations or poses) and the current states by providing a feedback loop that the system can compare some attributes associated with the current pose of the location sensor with a desired location sensor pose.

FIG. 7 is a block diagram showing a method 700 for automatically calibrating an endoscope (e.g., the endoscope 110 of FIG. 1) such that, for example, a transform between the coordinate frames for a location sensor (e.g., the location sensor 114 of FIG. 1) and camera (e.g., the camera 112 of FIG. 1) is determined. As FIG. 7 shows, the method 700 may include a first phase 702. During the first phase 702, the automatic calibration system may generate a location-sensor-to-robot-base transform. In embodiments where the location sensor is an EM sensor, the location-sensor-to-robot-base transform may be a field-generator-to-robot-base transform. The first phase 702 may involve a number of sub-blocks, which collectively represent the first phase 702 of a multiphase approach. For example, the first phase 702 may include sub-blocks 702a, 702b, and 702c. At sub-block 702a, the automatic calibration system may robotically command a first movement between the endoscope and a calibration pattern device (e.g., the calibration pattern device

120 of FIG. 1) to achieve one or more robotic poses in a robot coordinate frame. As used herein, the set of one or more robotic poses may be commanded and expressed using coordinates of the robotic coordinate frame. For example, the robotic controller may issue commands to a robotic arm to move the endoscope to a given location in the robotic coordinate frame (e.g., commands to move to a given x, y, z position and/or yaw, pitch, roll orientation of the robotic coordinate frame). Likewise, a robotic controller may issue commands to a robotic arm to move the calibration pattern device to a given location in a robotic coordinate frame (e.g., commands to move to a given x, y, z position and/or yaw, pitch, roll orientation of the robotic coordinate frame). In some embodiments, the robotic poses may be selected such that that the location sensor of the endoscope is fully within an operating portion of an EM field generated by a EM field generator (with, as described above, may be part of the calibration pattern device 120 of FIG. 1).

At sub-block 702*b*, the automatic calibration system may record robotic pose data and corresponding first location sensor pose data at each of the one or more robotic poses achieved at sub-block 702*a*. As discussed above, the location sensor pose data may be data that is operable to identify a pose (or at least some aspect thereof) of the location sensor in a location sensor coordinate frame. For example, in some embodiments, the automatic calibration system may derive location sensor pose data from the reading of the location sensor obtained at one of the robotic poses of sub-block 702*a*.

Accordingly, the automatic calibration system may store N pairs of robotic pose data and location sensor pose data, where N is the number of robotic poses achieved at sub-block 702*a*. The robotic pose data stored at sub-block 702*b* may be the robotic pose of the command sent to the robotic controller. In other embodiments, there may be some sensor feedback that estimates the pose of the robotic system, such as external cameras, EM sensors embedded in the robot, and the like.

The automatic calibration system, at sub-block 702*c*, calculates the location-sensor-to-robot-base transform using the pairs of robotic pose data (or transforms thereof) and the corresponding location sensor pose data (or transforms thereof), as was recorded at sub-block 702*b* (e.g., the first location sensor pose data). Generating a location-sensor-to-robot-base transform may involve collecting paired measurements of field generator to EM transforms and pairs of robot transforms and solving:

$$RX_{RL}=X_{RL}A$$

In this calculation, R represents the relative transforms between two robot poses (e.g., $R_1$, $R_2$) and may be defined as $R=R_2\_inv*R_1$. A represents a relative transform two location sensor poses ($A_1$, $A_2$) and can be defined as $A=A_2\_inv*A_1$. As described above, robotic poses may be represented as transformation from a robot base to an end effector (as may be determined using forward kinematics of the robot). Location sensor poses may be transformations from a measured location (e.g., location-sensor-to-field-generator). Thus, $R_1$ may be the transformation from a robot base to an end effector for the first pose, $A_1$ may be the transformation from location sensor for the first pose, $R_2$ may be the transformation from the robot base to end effector for the second pose, $A_2$ may be the transformation from the location sensor to the second pose pattern for the second pose. ($R_1$, $A_1$) and ($R_2$, $A_2$) are paired meaning synchronized. There are also probabilistic methods that use a batch of data where R, A pairs don't have to be synchronized.

During the second phase 704, the automatic calibration system may generate a location-sensor-to-camera transform (or a camera-to-location-sensor transform). The second phase 704 may involve a number of sub-blocks, such as, for example, sub-blocks 704*a*, 704*b*, and 704*c*. At sub-block 704*a*, the automatic calibration system may robotically command, using the location-sensor-to-robot-base transform generated during the first phase 702, a second movement between the endoscope and the calibration pattern device to achieve one or more location sensor poses in a location sensor coordinate frame. As previously mentioned, a location sensor pose may be expressed using coordinates of the location sensor coordinate frame. For example, the set of one or more location sensor poses of sub-block 704*a* may be expressed as the readings from the location sensor.

It is to be appreciated that sub-block 704*a* may operate by commanding robotic motions between the calibration pattern device and the endoscope such that determinable location sensor poses in a location sensor coordinate frame are achieved. However, the location sensor coordinate frame is a different coordinate frame from the robotic coordinate frame. To illustrate this difference, say the automatic calibration system determines that the location sensor needs to move left 50° in a location sensor coordinate frame to achieve a desired location sensor pose. If the automatic calibration system commands to a robotic controller to move left 50° this movement will occur in the robotic coordinate frame and this movement can result in moving the location sensor left at some other angle in the location sensor coordinate frame. Thus, in normal operation, a movement needed to move a current location sensor pose to a desired location sensor pose does not necessarily translate as the same movement in the robot coordinate frame. The location-sensor-to-robot-base transform facilities this operation in that the automatic calibration system can map movements in the location sensor coordinate frame to movements in the robotic coordinate frame. This approach is referred to as a location sensor servo approach and is described in greater detail below.

At sub-block 704*b*, the automatic calibration system may record second location sensor pose data and corresponding camera pose data at each of the one or more location sensor poses. As discussed above, the camera pose data may be data that is operable to identify a pose (or at least some aspect thereof) of the camera in the camera coordinate frame. Accordingly, the automatic calibration system may store pair N pairs of camera pose data and location sensor pose data, where n is the number of location sensor poses reached at sub-block 704*a*.

At sub-block 704*c* the automatic calibration system calculates a camera-to-location-sensor transform using the pairs of camera pose data (or transforms thereof) and the corresponding location sensor pose data (or transforms thereof), as was recorded at sub-block 704*b*. Generating a camera-to-location-sensor transform may involve collecting paired measurements of field generator to EM transforms and pairs of pattern-to-camera transforms and solving:

$$AX_{C2LS}=X_{C2LS}B$$

Where A represents relative transforms between location sensor poses (e.g., location-sensor-to-field-generator transforms, where the location sensor is an EM sensor) of the second phase 704, B represents the relative transforms between pattern poses of the second phase 704, and $X_{C2LS}$ represents the camera-to-location-sensor transform.

At block 706, the automatic calibration system stores data indicative of the camera-to-location-sensor transform in a computer-readable medium of the endoscope, such as the calibration data store 116 of FIG. 1. As discussed above, with respect to FIG. 1, a calibration data store may be an RFID tag but could be any suitable device capable of storing data indicative of the camera-to-location-sensor transform and then communicating the camera-to-location-sensor transform to a robotic system when the endoscope is coupled to the robotic system. Based on the camera-to-location-sensor transform, any camera pose, location sensor pose, or robotic pose may be specified or otherwise provided in any of the camera coordinate system, location sensor coordinate system, or robotic coordinate system. In some examples, any camera pose, location sensor pose, or robotic pose may be specified or otherwise provided in an EM coordinate frame, which may be the coordinate frame of the location sensor.

Figure 8:
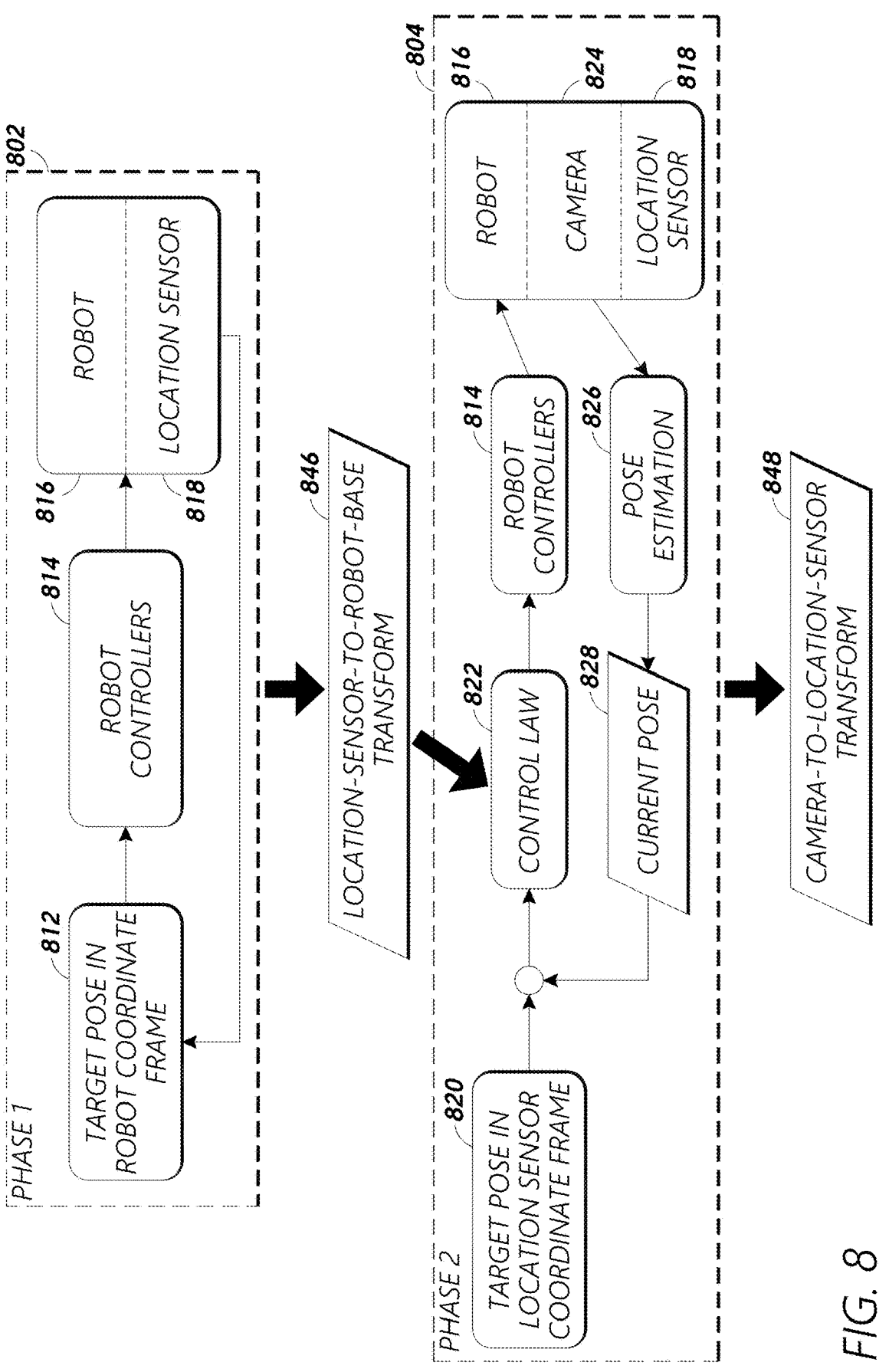
FIG. 8 is a block diagram illustrating an example embodiment of an automatic calibration system implementing a method for location sensor servo-based calibration.

FIG. 8 is a block diagram illustrating an example embodiment of an automatic calibration system 800 implementing a method for location sensor servo-based calibration. As FIG. 8 shows, the automatic calibration system 800 operates to perform multiple phases, a first phase 802 and a second phase 804, where the first phase 802 operates to generate a location-sensor-to-robot-base transform 846 and the second phase 804 operates to generate a location-sensor-to-camera transform 848. In the first phase 802, to obtain the location-sensor-to-robot-base transform 846, a set of robotic poses 812 in the robot coordination frame can be pre-determined empirically. It is worth noting that, depending on the type of location-sensor utilized by the automatic calibration system, it may be beneficial to select robotic poses that allow the location sensor to generate pose data that is indicative the pose of the sensor. For example, in embodiments utilizing EM sensors, the robotic poses ought to result in the EM sensors being located within a detectable region of the field generator. The robotic controller 814 issues commands to the robot 816 to move the endoscope to a given location in the robotic coordinate frame (e.g., commands to move to a given x, y, z position and/or yaw, pitch, roll orientation of the robotic coordinate frame).

After executing each robot pose 812, the corresponding robot pose and location sensor pose data are recorded. For example, after reaching a robotic pose, the robotic pose data associated with the robotic pose (e.g., position and/or orientation in 6DOF) are stored with location sensor pose data obtained at the robotic pose. With the obtained pairs of robotic pose data and location sensor data, the location-sensor-to-robot-base transform 846 is calculated.

In the second phase 804, the automatic calibration system uses the location-sensor-to-robot-base transform 846 generated in the first phase 802 to perform location sensor servo-based calibration to generate a location-sensor-to-camera transform 848. In location sensor servo-based calibration, the automatic calibration system may command robotic movement to perform 6-DOF motion relative to the location sensor such that the automatic calibration system can record pairs of location sensor pose data and camera pose data. For example, at block 820, the automatic calibration system selects a target location sensor pose from a set of location sensor poses (e.g., $\{A_i\}_{i=1}^n$).

For simplicity of discussion, the target location sensor pose is referred to as $A_t$. The target location sensor pose $A_t$ is then sent as input to the control law module 822.

The control law module 822 also receives a current location sensor pose 828 (referred to as $A_c$ for simplicity of discussion) from a feedback path where the current location sensor pose is determined (e.g., at block 826) from the location sensor 818.

It should be appreciated that the feedback loop of elements 822, 814, 816, 818, 826, 828 are repeated until the automatic calibration system determines that the current pose $A_c$ and the target pose $A_t$ are sufficiently similar (e.g., the target pose has been reached), as may be determined, for example, by a comparison of the difference between the current pose $A_c$ and the target pose $A_t$ is within a threshold amount.

Once the automatic calibration system determines that the target location sensor pose has been reached, the automatic calibration system may then record the image pose data (e.g., $B_i$). The next target pose is selected and the process is repeated to record a corresponding image pose data until a sufficient number of target location sensor poses have been reached and corresponding camera pose data recorded.

Thus, for the set of location sensor poses, the system will record corresponding image sensor poses. A location-sensor-to-camera transform is then generated using methods similar to those described above with reference to FIG. 7.

Implementing Systems and Terminology

Implementations disclosed herein provide systems, methods and apparatus for calibration of robotically controlled or user-controlled medical instruments. Various implementations described herein provide for improved calibration between location sensors and cameras embedded within or otherwise configured to be coupled with a medical instrument.

The automatic calibration system 100 can include a variety of other components. For example, the automatic calibration system 100 can include one or more control electronics/circuitry, power sources, pneumatics, optical sources, actuators (e.g., motors to move the robotic arms), memory, and/or communication interfaces (e.g. to communicate with another device). In some embodiments, the memory can store computer-executable instructions that, when executed by the control circuitry, cause the control circuitry to perform any of the operations discussed herein. For example, the memory can store computer-executable instructions that, when executed by the control circuitry, cause the control circuitry to receive input and/or a control signal regarding manipulation of the robotic arms and, in response, control the robotic arms to be positioned in a particular arrangement.

The various components of the automatic calibration system 100 can be electrically and/or communicatively coupled using certain connectivity circuitry/devices/features, which can or may not be part of the control circuitry. For example, the connectivity feature(s) can include one or more printed circuit boards configured to facilitate mounting and/or interconnectivity of at least some of the various components/circuitry of the automatic calibration system 100. In some embodiments, two or more of the control circuitry, the data storage/memory, the communication interface, the power supply unit(s), and/or the input/output (I/O) component(s), can be electrically and/or communicatively coupled to each other.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method to automate calibration of an endoscope of a robotic medical system, comprising:
   robotically commanding first movement between the endoscope and a calibration pattern to achieve one or more robotic poses in a robot coordinate frame;
   at each respective robotic pose from the one or more robotic poses, recording robotic pose data and corresponding first camera pose data;
   calculating a camera-to-robot-base transform based on the robotic pose data and the corresponding first camera pose data recorded at each respective robotic pose from the one or more robotic poses;
   robotically commanding, using the camera-to-robot-base transform, second movement between the endoscope and the calibration pattern to achieve one or more camera poses in a camera coordinate frame;
   at each respective camera pose from the one or more camera poses, recording second camera pose data and corresponding location sensor pose data;
   calculating a location-sensor-to-camera transform based on the second camera pose data and the corresponding location sensor pose data recorded at each respective camera pose from the one or more camera poses; and
   storing data indicative of the location-sensor-to-camera transform in a computer-readable medium configured to be coupled to the endoscope.

2. The method of claim 1, wherein robotically commanding the first movement between the endoscope and the calibration pattern comprises commanding robotic movement of the calibration pattern.

3. The method of claim 1, wherein robotically commanding the first movement between the endoscope and the calibration pattern comprises commanding robotic movement of the endoscope.

4. The method of claim 1, wherein the endoscope includes a location sensor, the location sensor includes at least one of: an electromagnetic sensor, a shape sensing fiber, an accelerometer, gyroscope, and a magnetometer.

5. The method of claim 1, wherein the computer-readable medium includes a radio frequency identification (RFID) tag configured to transmit the location-sensor-to-camera transform to a RFID reader disposed on the robotic medical system.

6. The method of claim 1, wherein the one or more camera poses each include desired feature locations corresponding to the calibration pattern.

7. The method of claim 1, wherein the one or more camera poses each include a position and orientation derived determinable from object point locations in an image and camera intrinsic parameters.

8. The method of claim 1, wherein robotically commanding the second movement between the endoscope and the calibration pattern to achieve the one or more camera poses in the camera coordinate frame comprises:
   estimating a current camera pose of the endoscope in the camera coordinate frame;
   determining a first motion to move the endoscope from the current camera pose towards a first camera pose, the first motion being in the camera coordinate frame;
   using the camera-to-robot-base transform, determining a second motion that corresponds to the first motion, the second motion being in the robot coordinate frame; and
   robotically commanding the endoscope to the one or more camera poses based on the second motion.

9. The method of claim 1, wherein robotically commanding the second movement between the endoscope and the calibration pattern to achieve the one or more camera poses in the camera coordinate frame comprises:
   estimating a current camera pose of the endoscope in the camera coordinate frame;
   determining a first motion to move the calibration pattern from the current camera pose towards a first camera pose, the first motion being in the camera coordinate frame;
   using the camera-to-robot-base transform, determining a second motion that corresponds to the first motion, the second motion being in the robot coordinate frame; and
   robotically commanding the calibration pattern to the one or more camera poses based on the second motion.

10. A method to calibrate an endoscope configured to be coupled to a robotic medical system, the method comprising:
   adjusting a relative position between the endoscope and a calibration pattern such that the endoscope and the calibration pattern are arranged according to a first determinable configuration;
   while at the first determinable configuration:
      recording first location data from a location sensor coupled to the endoscope, and
      recording first camera data from a camera coupled to the endoscope;
   adjusting the relative position between the endoscope and the calibration pattern such that the endoscope and the calibration pattern are arranged according to a second determinable configuration different from the first determinable configuration;
   while at the second determinable configuration:
      recording second location data from the location sensor coupled to the endoscope, and
      recording second camera data from the camera coupled to the endoscope;
   generating a location-sensor-to-camera transform based on the first location data, the first camera data, the second location data, and the second camera data; and
   storing data indicative of the location-sensor-to-camera transform on a computer-readable medium configured to be coupled to the endoscope.

11. The method of claim 10, wherein adjusting the relative position between the endoscope and the calibration pattern such that the endoscope and the calibration pattern are arranged according to the first determinable configuration comprises:
   moving the calibration pattern relative to the endoscope.

12. The method of claim 11, wherein moving the calibration pattern relative to the endoscope comprises:

manual adjustment of a positioning of the calibration pattern.

13. The method of claim 11, wherein moving the calibration pattern relative to the endoscope comprises:

robotic adjustment of a positioning of the calibration pattern.

14. The method of claim 10, wherein adjusting the relative position between the endoscope and the calibration pattern such that the endoscope and the calibration pattern are arranged according to the first determinable configuration comprises:

moving the endoscope relative to the calibration pattern.

15. The method of claim 14, wherein moving the endoscope relative to the calibration pattern comprises:

manual adjustment of a positioning of the endoscope.

16. The method of claim 10, wherein the location sensor includes at least one of: an electromagnetic sensor, a shape sensing fiber, an accelerometer, gyroscope, and a magnetometer.

17. The method of claim 10, wherein the computer-readable medium includes a radio frequency identification (RFID) tag configured to transmit the location-sensor-to-camera transform to a RFID reader disposed on the robotic medical system.

18. The method of claim 10, wherein the location sensor includes an electromagnetic sensor configured to generate the first location data based on a positioning relative to an electromagnetic field generator, and the calibration pattern being located on an electronic field generator.

19. The method of claim 18, wherein movement of the field generator causes changes in: (a) a relative placement between the location sensor and the electronic field generator and (b) a relative placement between the camera and the calibration pattern.

20. A system to automate calibration of an endoscope, the system comprising:

a robotic arm configured to facilitate movement between the endoscope and a calibration pattern;

control circuitry; and a memory storing computer-executable instructions, that when executed, cause the control circuitry to:

robotically command the robotic arm to facilitate first movement between the endoscope and the calibration pattern to achieve one or more robotic poses in a robot coordinate frame, at each respective robotic pose from the one or more robotic poses, record robotic pose data and corresponding first location sensor pose data, calculate a location-sensor-to-robot-base transform based on the robotic pose data and the corresponding first location sensor pose data recorded at each respective robotic pose from the one or more robotic poses, robotically command, using the location-sensor-to-robot-base transform, the robotic arm to facilitate second movement between the endoscope and the calibration pattern to achieve one or more location sensor poses in a location sensor coordinate frame, at each respective location sensor pose from the one or more location sensor poses, record second location sensor pose data and corresponding camera pose data, calculate a location-sensor-to-camera transform based on the second location sensor pose data and the corresponding camera pose data recorded at each respective location sensor pose from the one or more location sensor poses, and store data indicative of the location-sensor-to-camera transform in a computer-readable medium configured to be coupled to the endoscope.

* * * * *